United States Patent [19]

Manzer

[11] 4,057,565
[45] Nov. 8, 1977

[54] 2-DIALKYLAMINOBENZYL AND 2-DIALKYLAMINOMETHYLPHENYL DERIVATIVES OF SELECTED TRANSITION METALS

[75] Inventor: Leo Ernest Manzer, Wilmington, Del.

[73] Assignee: E. I. Du Pont de Nemours and Company, Wilmington, Del.

[21] Appl. No.: 597,981

[22] Filed: July 22, 1975

[51] Int. Cl.² .............. C07F 5/00; C07F 7/00; C07F 7/28; C07F 11/00
[52] U.S. Cl. .............. 260/429 R; 252/431 N; 260/429.2; 260/429.3; 260/429.5; 260/438.5 R; 260/568; 526/159
[58] Field of Search ............. 260/429.3, 429.5, 429 R, 260/438.5 R, 439 R, 429.2, 429 J

[56] References Cited

U.S. PATENT DOCUMENTS 3,813,423  5/1974  Pioli et al. .................. 260/429.3

FOREIGN PATENT DOCUMENTS 1,336,779  11/1973  United Kingdom.

OTHER PUBLICATIONS

Chemical Abstracts, v78, 43718t (1973).
Bahr et al., Angew. Chem. 75, p. 94 (1963).
Joseph et al., Indian J. Chem. vol. 8, p. 464 (1970).
Cope et al., J. Organometal Chem. 8 (3) pp. 527–533 (1967).
Chemical Abstracts, 29, 7299⁷ (1935).
Longoni et al., J. Organometal Chem., 39, pp. 413–425 (1972).
Ytsma et al., J. Organometal Chem., 74, pp. 239–244 (1974).

Primary Examiner—Helen M. S. Sneed

[57] ABSTRACT

Transition metal compounds of the formulae $$M^1A_3 \quad (1)$$

wherein
  $M^1$ is scandium, yttrium, chromium, or rare earth metal, and
  A is 2-dialkylaminobenzyl or 2-dialkylaminomethylphenyl, or a lower alkyl derivative thereof, $$M^2A_2 \quad (2)$$

wherein
  $M^2$ is Cr or Mo and $$M^3A_4 \quad (3)$$

wherein
  $M^3$ is Ti, Zr or Hf
are useful as components of coordination catalysts for olefin polymerization. Lithium compounds of the formula LiA are intermediates used in preparing the above compounds. All of the above compounds are also useful as oxygen-scavenging agents.

11 Claims, No Drawings

2-DIALKYLAMINOBENZYL AND 2-DIALKYLAMINOMETHYLPHENYL DERIVATIVES OF SELECTED TRANSITION METALS

BACKGROUND OF THE INVENTION

1. Field of the Invention

This invention relates to new organometallic derivatives of selected transition metals and lithium. It also relates to the use of the new transition-metal compounds as components of coordination catalyst systems for polymerizing olefins.

2. Description of the Prior Art

In British Pat. No. 1,336,779 Longoni et al. disclose compounds of the formula

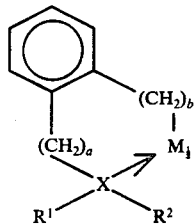

where X is nitrogen or phosphorus; M is nickel, palladium, or platinum; $R^1$ and $R^2$ are the same or different and are alkyl; $a$ is 0 or 1; $b$ is 0 or 1; and $a + b$ is 1. In all specific compounds disclosed in which $b$ is 1, X is phosphorus. The nickel derivative catalyzed the oligomerization and the cyclo-oligomerization of butadiene. Specific compounds disclosed in which $a$ is 1 are the bis(2-dimethylaminomethylphenyl) derivatives of nickel, palladium, and platinum. The nickel and palladium derivatives catalyzed the hydrogenation of cyclohexene.

In *Angew. Chem.*, 75, 94 (1963), Bahr and Zohm disclose reaction of chromium trichloride with 2-diethylaminomethylphenyllithium to give tris(2-diethylaminomethylphenyl)chromium. The product was highly unstable to atmospheric oxygen.

In *J. Organometal Chem.*, 8, (3), p. 527 (1967) Cope and Gourley teach the preparation of 2-dimethylaminomethylphenyllithium and 5-t-butyl-2-dimethylaminomethylphenyllithium from butyllithium and the corresponding benzylamines. Reaction of these lithium derivatives with cobalt(II) chloride gave the corresponding tris(aminomethylphenyl)cobalt(III) compounds. Tris(5-t-butyl-2-dimethylaminomethylphenyl)cobalt(III) is described as "stable when kept at room temperature in air".

In *J. Organometal Chem.*, 39, p. 413 (1972) Longoni et al. teach the preparation of bis(2-dimethylaminomethylphenyl) derivatives of nickel, palladium, and platinum, together with the corresponding diethylamino compounds, from the corresponding lithium derivatives and the metal halides. 2-Diethylaminomethylphenyllithium was prepared from butyllithium and 2-bromo-N,N-diethylbenzylamine.

In *J. Organometal Chem.*, 74, p. 239 (1974) Ytsma et al. teach the preparation of dicyclopentadienyl (2-dimethylaminomethylphenyl)titanium(III) and the corresponding vanadium(III) compound from the dicyclopentadienylmetal(III) chlorides and 2-dimethylaminomethylphenyllithium. They reacted immediately with oxygen to give unidentified products.

SUMMARY OF THE INVENTION

The present invention is directed to transition metal compounds of the formula

wherein
$M^1$ = Sc, Y, or rare earth metal, and

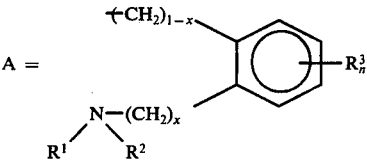

wherein
$x = 0$ or 1
$R^1$, $R^2$ and the $R^3$'s are each $C_1$-$C_8$ alkyl, and
$n = 0, 1, 2, 3,$ or $3 + x$,
when $x = 0$, the position in the benzene ring adjacent to the —$NR^1R^2$ substituent, other than that occupied by the —$CH_2$— substituent, being unsubstituted,

wherein $M^2$ = Cr or Mo, and

wherein
$M^3$ = Ti, Zr or Hf,
there being a coordination bond between $M^1$, $M^2$ or $M^3$ and the nitrogen of A.

This invention is also directed to lithium compounds of the formula

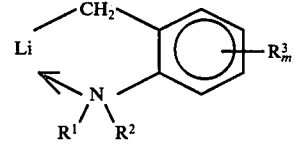

wherein
$R^1$, $R^2$ and the $R^3$'s are each $C_1$-$C_8$ alkyl, and
$m = 0, 1, 2$ or 3, the position in the benzene ring adjacent to the —$NR^1R^2$ substituent, other than that occupied by the —$CH_2$— substituent, being unsubstituted.

This invention is also directed to a method of polymerizing olefins which comprises contacting a. an olefin selected from the group consisting of 1-alkenes of 2 to about 10 carbons and mixtures thereof, b. a transition metal compound of one of the formulae

wherein
$M^4$ = Sc, Y, Cr, or rare earth metal, and

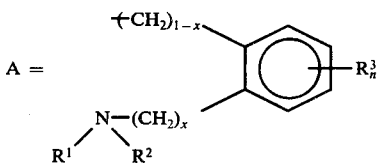

wherein x = 0 or 1

$R^1$, $R^2$ and the $R^3$'s are each $C_1-C_8$ alkyl, and n = 0, 1, 2, 3 or 3 + x, when x = 0, the position in the benzene ring adjacent to the —$NR^1R^2$ substituent, other than that occupied by the —$CH_2$— substituent, being unsubstituted, $$M^2A_2 \qquad (2)$$

wherein $M^2$ = Cr or Mo, and $$M^3A_4 \qquad (3)$$

wherein $M^3$ = Ti, Zr or Hf, there being a coordination bond between $M^4$, $M^2$ or $M^3$ and the nitrogen of A, (c) an organoaluminum compound selected from the group consisting of trialkylaluminums, dialkylaluminum hydrides, dialkylaluminum alkoxides, alkylaluminum halides and polymeric hydrocarbylaluminums in which the alkyl groups, alike or different, have 1–10 carbons each in an inert, liquid hydrocarbon diluent in a mole ratio of organoaluminum compound to transition metal compound of about 1000:1 to 4:1 with agitation at a temperature of 0°–250° C and a pressure from atmospheric to 500 atmospheres thereby forming polyolefin.

DETAILED DESCRIPTION OF THE INVENTION

One class of the transition metal compounds of this invention are the trivalent transition metal compounds of the formula $$M^1A_3$$

wherein $M^1$ is Sc, Y, or rare earth metal. The preferred trivalent transition metal compounds are those in which $R^1$ and $R^2$ are the same and n is not more than 1. Suitable $C_1-C_8$ alkyl groups, as R groups, include methyl, ethyl, isopropyl, s-butyl, t-pentyl, hexyl, isoheptyl, octyl, and 2-ethylhexyl. Most preferably these substituents are methyl.

The trivalent transition metal compounds are prepared by reacting the corresponding lithium compound of the formula LiA with the corresponding transition metal chloride of the formula $$M^1Cl_3$$

A typical reaction is as follows:

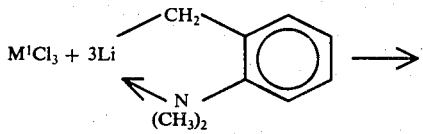

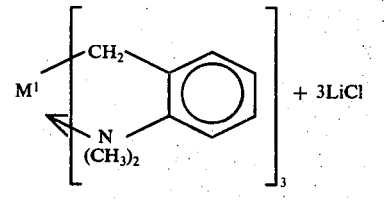

The 2-dialkylaminobenzyllithium compounds can be prepared by reacting the corresponding N,N-dialkyl-o-toluidine with an alkyllithium such as butyllithium in accordance with the equation:

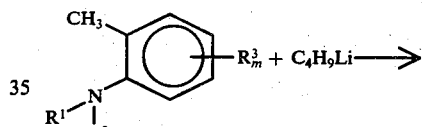

Suitable 2-dialkylaminobenzyllithiums include 2-dimethylaminobenzyllithium, 2-diethylamino-5-methylbenzyllithium, 2-dibutylaminobenzyllithium, 2-(N-hexyl-N-methylamino)benzyllithium, 2-dioctylaminobenzyllithium, 2-diethylamino-4,6-diethylbenzyllithium, and 2-dimethylamino-4,5,6-trimethylbenzyllithium.

The 2-dialkylaminomethylphenyllithium compounds can be prepared by the methods of Cope and Gourley, J. Organometal Chem., 8, 527 (1963). As shown in this reference, the precursor N,N-dialkylbenzylamines containing one or more alkyl substituents on the benzene ring are prepared starting with an alkyl-substituted benzoic acid containing no substitution in at least one position ortho to the carboxylic group. The acid is converted via its acid chloride to the appropriate N,N-dialkylbenzamide, which is reduced with lithium aluminum hydride to the amine. Reaction with an alkyllithium gives the 2-dialkylaminomethyllithium:

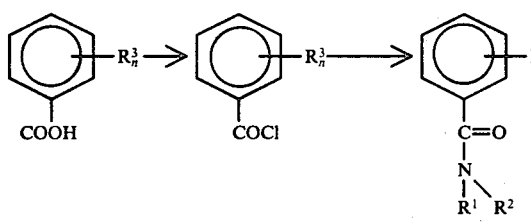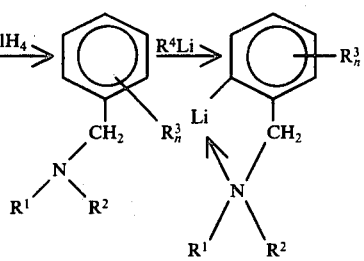

Suitable 2-dialkylaminomethylphenyllithiums include 2-dimethylaminomethylphenyllithium, 5-t-butyl-2-dimethylaminomethylphenyllithium, 2-dipentylaminomethylphenyllithium, 2-dimethylaminomethyl-4,6-diethylphenyllithium, 2-dimethylaminomethyl-5-octylphenyllithium, and 2-(N-ethyl-N-octylaminomethyl)phenyllithium.

A second class of the transition metal compounds of this invention are the divalent transition metal compounds of the formula $M^2A_2$ wherein $M^2$ is Cr or Mo. The preferred divalent transition metal compounds are those in which $R^1$ and $R^2$ are the same and $n$ is not more than 1. These compounds are prepared by reacting the corresponding lithium compound of the formula LiA with $MoCl_3$, or the dichloride or diiodide of chromium.

With certain amines and phosphines the divalent transition metal compounds of the formula $M^2A_2$ form complexes in which two nitrogen or phosphorus atoms are bonded to the transition metal. Examples of complexing ligands are bipyridine, ethylenebis(dimethylphosphine), ethylenebis(diethylphosphine), and trimethylphosphine. In addition, in the course of their preparation in solvents such as tetrahydrofuran, these products are involved in readily dissociable complexes having the composition $M^2A_2 \cdot$ (lithium halide)$_2 \cdot$ (tetrahydrofuran)$_2$.

A third class of the transition metal compounds of this invention are the tetravalent transition metal compounds of the formula $M^3A_4$ where $M^3$ is Ti, Zr or Hf. The preferred tetravalent transition metal compounds are those in which $R^1$ and $R^2$ are the same and $n$ is not more than 1. These compounds are prepared by reacting the corresponding lithium compound of the formula LiA with $TiCl_4$, $ZrCl_4$ or $HfCl_4$.

It has been further discovered in accordance with this invention that the novel transition metal compounds of this invention, as well as chromium compounds of the formula $CrA_3$, are useful as coordination catalyst components in the polymerization of olefins. The polymerization is carried out by contacting an olefin with the transition metal compound and an organoaluminum compound in an inert liquid hydrocarbon diluent with agitation until the polyolefin is formed. The preferred transition metal compounds for this use are those in which $M^1$ is Sc, Y, or Cr.

The coordination catalyst system used in the polymerization reaction includes the transition metal compound and an organoaluminum compound selected from the group consisting of trialkylaluminums ($R^1R^2R^3Al$), dialkylaluminum hydrides ($R^1R^2AlH$), dialkylaluminum alkoxides ($R^1R^2AlOR^3$), alkylaluminum halides ($R^1R^2AlX$ and $R^1AlX_2$) and polymeric hydrocarbylaluminums in which the alkyl groups, alike or different, have 1 to about 10 carbon atoms each. Suitable compounds include the commercially available trimethylaluminum, triethylaluminum, tri-n-propylaluminum, triisobutylaluminum, tri-n-hexylaluminum, tri-n-octylaluminum, tri-n-decylaluminum, diethylaluminum hydride, diisobutylaluminum hydride, diethylaluminum ethoxide, diisobutylaluminum ethoxide, and the like. Polymeric hydrocarbylaluminums such as aluminum-isoprene polymers are described in U.S. Pat. No. 3,149,136. The trialkylaluminums and dialkylaluminum hydrides are preferred. The alkylaluminum halides are not preferred since the final polymer is corrosive to metal in many applications. Preferably the resulting polymer is free of residual halogen and thus noncorrosive.

Suitable inert, liquid, hydrocarbon diluents for use as the polymerization medium include aromatic, saturated aliphatic, and saturated alicyclic hydrocarbons. While liquid hydrocarbons of about 5–10 carbons such as pentane, hexane, heptane, octane, decane, cyclohexane, benzene, toluene, xylene and tetralin are preferred, the lower-boiling propanes and butanes can also be used.

The diluent should be anhydrous and preferably is made so by passing it through highly absorptive alumina such as a Woelm acid alumina column immediately prior to use. The liquid diluents can also be freed of contaminants such as oxygen and water by treatment with traces, e.g., about 0.50%, based on the weight of diluent, of the organoaluminum compound to be used as a catalyst component in the polymerization. This, along with the acid alumina treatment, ensures maximum avoidance of moisture and other impurities.

The olefins that are operable in this process are 1-alkenes of 2 to about 10 carbons and combinations of two or more such monomers with each other. Suitable monomers include ethylene, propylene, 1-butene, 1-pentene, 3-methyl-1-butene, 4-methyl-1-pentene, 1-hexene, 1-octene, 1-decene, and mixtures thereof. Particularly preferred are ethylene, propylene and combinations of ethylene with up to about 15% by weight of one or more 1-alkenes of 3 to about 10 carbons. Other monomers known to be reactive in coordination polymerization reactions, for example, linear, nonconjugated diolefins such as 1,4-hexadiene, 1,6-octadiene, dicyclopentadiene, norbornene and norbornene derivatives such as ethylidenenorbornene, may also be added in small amounts. The most preferred monomer is ethylene.

The polymerization reaction can be carried out at temperatures of about 0°–250° C. Polymerization temperatures below that at which the diluent swells the polyolefin are preferred since swelling greatly increases the viscosity of the reaction mixture and makes agitation difficult or impossible unless low concentrations of materials are used. For practical reasons, the polymerization should be run at temperatures not in excess of about 100° C. when pure alkanes or cycloalkanes are used. When a strong polyolefin solvent such as benzene, toluene, tetralin, or xylene is used, even lower temperatures such as about 60° C. or below should be used. Preferably temperatures of about 25°–100° C. are used, and most preferably about 50°–90° C.

Polymerization is readily carried out at pressures from about atmospheric to about 500 atmospheres. Pressures in the lower range are generally preferred, and about 3–70 atmospheres are most satisfactory. A supply vessel is normally used to maintain the pressure in the reaction vessel. Reaction times may vary over a wide range, for example, from a few seconds to about 24 hours.

In a preferred embodiment of the present invention the polymerization reaction is carried out by dispersing at least about 1 weight/volume percent and preferably about 5 weight/volume percent of an inorganic filler compound in an inert, liquid hydrocarbon along with the transition metal compound and the organoaluminum compound. The olefin is then added and the polymerization is carried out until a composite containing about 10–70% by weight, based on the polyolefin and filler, of polyolefin is formed. Weight/volume percent, as used throughout the specification and claims, refers to grams of solid added to 100 milliliters of liquid.

Any inorganic filler compound can be used in this preferred process. Suitable fillers include minerals, for example, alumina hydrates such as alumina trihydrate and the like; metal phosphates and sulfates such as insoluble calcium phosphates, calcium sulfate, and barium sulfate; silicas ($SiO_2$) such as sand, diatomaceous earth and pumice; metal carbonates such as barium carbonate, calcium carbonate and zinc carbonate; metal oxides such as titania (e.g., rutile and anatase), zinc oxide, antimony oxide, and iron oxide (e.g., magnetite $FeO.Fe_2O_3$); and water-insoluble silicates including calcium silicates ($CaSiO_3$) such as wollastonite, magnesium silicates such as talc, magnesium calcium aluminum silicates [$(Mg.Ca)O.Al_2O_3.5SiO_2.nH_2O$] such as montmorillonite and serpentine, lithium aluminum silicates such as spodumene [$(Li,Na)_2Al_2Si_4O_{12}$], potassium aluminum silicates such as feldspar ($K_2O.Al_2O_3.6SiO_2$) and mica ($K_2O.3Al_2O_3.6SiO_2.2H_2O$), magnesium iron silicates such as olivine [$(Mg,Fe)_2SiO_4$], aluminum silicates ($Al_2O_3.SiO_2$) such as sillimanite and kyanite, and aluminum silicate clays such as kaolinite, attapulgite, fuller's earth and bentonite; and natural mixtures of these compounds such as slate. Other suitable inorganic fillers include synthetic silicas; synthetic carbonates; glass powder and fibers; synthetic silicates such as "Silene" L, a precipitated hydrated calcium silicate; synthetic titanates such as "Fybex", an acicular potassium titanate; synthetic carbon such as carbon black.

The filler used in this preferred embodiment should have a weight-average equivalent spherical particle diameter of about 0.1 to about 50 μ. The term "equivalent spherical particle diameter" is used because not all of the useful fillers are spherical in shape and thus do not have simple diameters. This term means that the particle has a diameter equivalent to the diameter of a sphere having the same volume. Preferably the weight-average equivalent spherical particle diameter is about 1 to about 25 μ. The filler should also have a surface area of about 0.01 to about 100 m²/g. Preferably the surface area is in the range of about 0.5 to about 50 m²/g.

The filler should have a neutral-to-acidic surface. Many fillers such as alumina hydrates, silicas, water-insoluble silicates, insoluble calcium phosphates, titania, zinc oxide, iron oxide, antimony oxide and mixtures thereof naturally have neutral-to-acidic surfaces. Other fillers such as calcium sulfate, calcium carbonate, barium sufate and zinc carbonate are basic in nature and thereby inhibit polymerization. Still other minerals such as mica, silicas which contain alkali metal or alkaline earth metal, and wollastonite give variable polymerization behavior.

In those cases where the filler is not neutral-to-acidic, it has been found that polymerization inhibition difficulties can be overcome by first coating the filler with about 0.01 to about 2%, based on the filler, of an acidic oxide such as silica, alumina or acid phosphate thereby giving the filler an acidic surface. More acidic oxide could be added but would serve no useful purpose. The amount of acidic oxide at the surface of the filler can vary from about 0.001 to about 0.5 millimole per gram of filler, and preferably about 0.01 to about 0.05 millimole.

These acidic oxide coatings are obtained by treating the filler with a compound which is hydrolyzed to an acidic oxide. For example, carbonate fillers are coated by simply mixing an aqueous suspension containing about 10–50% by weight of the solid filler with an aqueous solution containing about 1–10% by weight of an aluminum salt:

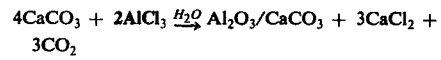

Other minerals can be coated by treating with an aqueous salt solution and ammonia:

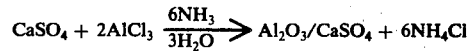

Acid phosphate coatings can be obtained by treating the filler with phosphoric acid:

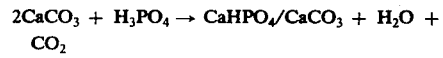

Silica coatings can be obtained, for example, by treating calcium carbonate with silicon tetrachloride:

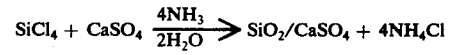

Before the filler can be used in the polymerization reaction, it must first be freed of gaseous oxygen, water and other polar impurities that interfere with the polymerization reaction. This is readily accomplished by sweeping the filler with an inert gas such as nitrogen with heating.

In this preferred embodiment of the polymerization reaction, the amount of organic transition metal compound added should be sufficient to provide about 0.00001 to about 0.05 millimole of transition metal per gram of filler and preferably about 0.0001 to about 0.01 millimole. This amount will provide filler having interacted at its surface sufficient organic transition metal compound to provide about 0.000001 to about 0.05 millimole of transition metal per gram of filler and preferably about 0.000001 to about 0.01 millimole. The organoaluminum compound should be present in the amount of about 0.001 to about 1.0 millimole per gram of filler and preferably about 0.002 to about 0.2 millimole. The mole ratio or organoaluminum compound to transition metal compound should be in the range of about 1000:1 to about 4:1 and preferably about 40:1 to about 10:1.

The polyolefin/filler composites prepared by this preferred embodiment have outstanding properties when they are prepared in such a way that the resulting composite is homogeneous. This can be accomplished with the subject transition metal compounds by controlling the order of addition of the transition metal compound and the organoaluminum compound so that polymerization takes place on substantially all of the filler particles. Since these catalysts are very active and are readily adsorbed by the filler, care must be taken that the catalyst is not all adsorbed by only part of the filler.

The most important principle relating to the preparation of homogeneous polyolefin/filler composites is that initial contact of the filler with catalyst must not be between the filler and the transition metal compound component of the catalyst system. Initial contact between the filler and the transition metal compound leads to a heterogeneous product and should be avoided.

In preparing homogeneous products by this approach, initial contact between the filler and the transition metal compound can be avoided by proceeding in one of two ways. In accordance with one method, the filler is first reacted with a large excess of the organoaluminum compound. The mole ratio of organoaluminum compound to transition metal compound should preferably be in the range of about 1000:1 to about 4:1 and most preferably about 40:1 to about 10:1.

It is believed that this excess organoaluminum compound reacts with many of the hydroxyl groups on the surface of the filler, thus limiting the adsorption sites available to the transition metal compound. The transition metal compound now reacts uniformly with all of the filler particles as it seeks the limited number of available sites.

In accordance with another method of avoiding initial contact between the filler and the transition metal compound, the transition metal compound is first reacted with a large excess of the organoaluminum compound in amounts which provide a mole ratio of organoaluminum compound to transition metal compound of about 1000:1 to about 4:1 thereby forming a complex. The dispersion of filler in the hydrocarbon diluent is then contacted with the complex in an amount sufficient to provide about 0.001 to about 1.0 millimole and preferably about 0.002 to about 0.2 millimole, per gram of filler, of organoaluminum compound and about 0.00001 to about 0.05 milligram-atom, and preferably about 0.0001 to about 0.01 milligram-atom, per gram of filler, of transition metal.

It is important that there be agitation during the polymerization reaction. Agitation controls both particle size and uniformity of composition. Strong agitation, as achieved with very rapid stirring, gives a fine-grained, free-flowing product. This is best achieved by use of an autoclave equipped with an efficient stirrer. The resulting polyolefin/filler composite is isolated as a free-flowing powder by means of conventional steps such as filtering, washing and drying.

The polyolefin/filler composites prepared in accordance with the preferred embodiment are formed into useful articles by various forming techniques which involve subjecting the composite to a temperature at which the composite softens in the range of about 105°–250° C and a positive pressure of about 10–100,000 psi or more. In general, temperatures of about 150°–225° C and pressure of about 10–15,000 psi are preferred.

A useful means of forming articles from these polyolefin/filler composites is by compression molding, which involves the simultaneous application of heat and pressure. This operation can be carried out by filling a mold with the composite powder, and pressing the powder in the mold with application of heat sufficient to raise the temperature above the softening point of the composite. Temperatures of about 150°–225° C. and positive pressures of about 10–5000 psi, and preferably at least about 1000 psi, are suitable. When the formed article has cooled below the melting point of the polymer, the mold is opened and the article is removed.

Sheets may be formed from these polyolefin/filler composites using suitable sheeting equipment by passing the composite along a continuous belt, subjecting the composite to a softening temperature in the range of about 150°–250° C. while it passes through a restricted space which compresses the composite against the belt at a pressure of about 50–5000 psi without subjecting the composite to shearing forces, and removing the resulting sheet from the continuous belt after it passes through the restricted space.

The reforming of these compression molded sheets can also be carried out by controlled hydraulic forming in which the elastomeric pad is a rubber diaphragm backed by a hydraulic fluid. Still another method of reforming is by hot or cold, matched-metal mold forming, that is, pressing or stamping the sheet between male and female metal dies at temperatures from ambient to about 250° C.

Because of the particulate nature of the composites prepared by the preferred process they are amenable to another method of forming objects, based on powder technology, which involves cold compressing in a mold followed by sintering. The powder is placed in a mold and compressed at a pressure of about 100–100,000 psi, preferably at least about 1000 psi, and most preferably, at least about 5,000 psi, at a temperature below the melting point of the polymer to form self-supporting articles. The article is then removed from the mold and densified by heating at a temperature above the softening point of the composite, e.g., about 105°–225° C., to form the finished article.

EXAMPLES OF THE INVENTION

Examples 1–17 illustrate the novel products of this invention and their preparation. Examples 18–37 illustrate the polymerization process of this invention. Example 38 illustrates the utility of the products of this invention as oxygen-scavenging agents.

In these examples all operations were carried out in an atmosphere of nitrogen. In Examples 18–37 triisobutylaluminum was used as a 1 M solution in heptane, and triethylaluminum, as a 1.6 M solution in heptane. Filler contents were calculated from ash contents on combustion. These calculations take into consideration the fact that all water of hydration is lost during combustion.

Physical properties reported in Examples 18–37 were determined by the following ASTM test designations.

| Property | Test Specifications |
| --- | --- |
| Tensile strength, maximum (T) | ASTM D-638-71A |
| Elongation at break ($E_b$) | ASTM D-638-71A |
| Modulus in tension, initial ($M_i$) | ASTM D-638-71A |
| Izod impact strength | ASTMD-256-72A |
| Gardner impact strength (falling dart) | SPI TS-159 |

In the tensile, elongation and modulus tests, test bars of Type I and Type V of ASTM test method 638-72 and bars prepared according to ASTM test method 638-44T were used.

Inherent viscosities of the polyethylene in the composite products were determined in 1,2,4-trichlorobenzene at 130° C. by placing a sample of the composite powder calculated to contain 0.025 g of polyolefin in a closed flask containing a magnetic stirring bar and adapted for insertion of a thermometer and a condenser containing a nitrogen purge tube. Into this flask is pipetted 50 ml of 1,2,4-trichlorobenzene containing 1.33 g/L of butylated hydroxytoluene anti-oxidant to give a 0.05 weight/volume percent solution of polyolefin.

With the thermometer and condenser in place, nitrogen is slowly passed over the contents of the flask, the magnetic stirrer is started, and the contents of the flask are heated to 180° C. The solution is stirred at this temperature for 2 hours. At the completion of this time, the condenser unit and the thermometer are removed from the flask. A ground glass stopper is inserted into the thermometer-well, a tube to support a capillary viscometer is inserted in the condenser-well, and the entire unit is transferred to an oil bath and maintained at 130° C. A capillary viscometer having three scratch marks, one near the bottom, one above the bulb and one below the bulb is inserted in the support tube.

After 1 hour at 130° C. in the oil bath, the viscometer is adjusted so that the tip is immersed in the solution to the depth indicated by the bottom scratch. Vacuum is gently applied to the top of the viscometer until the solution has risen to a level above the top scratch on the viscometer. The vacuum is removed and the solution is allowed to fall. The flow of the solution between the scratch above the bulb and the scratch below the bulb is timed. This flow time measurement is repeated until three values which check within ± 0.3 second are obtained. The flow time of the pure solvent is also measured at 130° C. in the same way.

The inherent viscosity is calculated using the following equations:

$$\text{Relative Viscosity} = \frac{\text{Time of solution}}{\text{Time of solvent flow}}$$

$$\text{Inherent Viscosity} = \frac{\text{natural log of relative viscosity}}{\text{w/v\% polymer concentration}}$$

EXAMPLE 1

This example illustrates the preparation of 2-dimethylaminobenzyllithium.

To a mixture of 23 ml of a 1.6 M solution of butyllithium in hexane and 10 ml of ethyl ether was added 5.0 g of N,N-dimethyl-o-toluidine with stirring. The mixture gradually became yellow and overnight a pale yellow solid was deposited. It was separated by filtration and dried, to give 2.0 g of 2-dimethylaminobenzyllithium.

EXAMPLE 2

This example illustrates another preparation of 2-dimethylaminobenzyllithium.

A mixture of 96.0 g of N,N-dimethyl-o-toluidine and 444 ml of a 1.6 M solution of butyllithium in hexane was stirred for two days. Stirring was stopped and the orange solution was cooled in ice until it became cloudy, whereupon stirring was resumed with continuing cooling. A yellow solid separated. Volatile materials were removed, about 50 ml of ethyl ether was added, and the solution was stirred for another 24 hours. During this time a large amount of solid separated. It was washed from the flask with pentane to give 2-dimethylaminobenzyllithium in 100% yield (mp above 200° C with decomposition). The infrared absorption spectrum of the product was in agreement with its assigned structure.

If butyllithium is reacted with N,N-diethyl-2,4-xylidine by essentially the method of Example 2, 2-diethylamino-5-methylbenzyllithium will be formed.

EXAMPLE 3

This example illustrates the preparation of tris(2-dimethylaminobenzyl)scandium.

To a stirred suspension of 2.0 g of anhydrous scandium trichloride in about 100 ml tetrahydrofuran was added, as a solid, 5.60 g of 2-dimethylaminobenzyllithium. The mixture was stirred overnight to give a red-orange solution. The tetrahydrofuran was removed by rotary evaporation to give an oil. The oil was dissolved in toluene and the solution was filtered. The toluene was removed by rotary evaporation, and about 50 ml of ethyl ether was added. The yellow crystals that separated were filtered off and washed with pentane. The yield of tris(2-dimethylaminobenzyl)scandium was 3.30 g (mp 115°–118° C).

Nmr ($C_6D_6$, 220 MHz): 6.93 ppm (4H, aromatic), 2.27 ppm (6H, N-Me), 1.64 ppm (2H, $CH_2$).

Anal. Calcd. for $C_{27}H_{36}NSc$: C, 72.45; H, 8.11; N, 9.39. Found: C, 70.72; H, 8.05; N, 9.56 70.76, 7.77, 9.74, 70.63, 8.07.

If yttrium trichloride is used in place of scandium trichloride in essentially the foregoing procedure, tris(2-dimethylaminobenzyl)yttrium will be formed.

If 2-diethylamino-5-methylbenzyllithium is reacted with scandium trichloride by the procedure of Example 3, tris(2-diethylamino-5-methylbenzyl)scandium will be produced.

EXAMPLE 4

This example illustrates the preparation of tris-(2-dimethylaminobenzyl)erbium.

To a stirred suspension of 2.0 g of erbium trichloride in tetrahydrofuran was added 3.10 g of 2-dimethylaminobenzyllithium. The mixture was stirred overnight, and the solvent was removed by rotary evaporation to give an orange solid. Toluene was added and the mixture was filtered. The filtrate was cooled to give large orange crystals that were filtered off and washed with pentane. The yield of tris(2-dimethylaminobenzyl)erbium was 1.85 g (mp 161°–163° C).

Anal. Calcd. for $C_{27}H_{36}N_3Er$: C, 56.90; H, 6.37; N, 7.37. Found (avge): C, 55.69; H, 6.21; N, 6.17.

If lanthanum trichloride is used in place of erbium trichloride in essentially the process of the fore-going example, tris(2-dimethylaminobenzyl)lanthanum will be formed.

EXAMPLE 5

This example illustrates the preparation of tris-(2-dimethylaminomethylphenyl)scandium.

To a suspension of 2.0 g of anhydrous scandium trichloride in 100 ml of tetrahydrofuran was added 5.60 g of 2-dimethylaminomethylphenyllithium as a solid. The mixture was refluxed for one hour and cooled. The white solid that had precipitated was separated by filtration and washed with 20 ml of tetrahydrofuran and then with 20 ml of ethyl ether. The combined washings and filtrate were stripped to dryness by rotary evaporation to give a further crop of white solid that was washed from the flask with tetrahydrofuran. The total yield of tris(2-dimethylaminomethylphenyl) scandium was 4.80 g (mp 180°–182° C).

Anal. Calcd. for $C_{27}H_{36}N_3Sc$: C, 72.46; H, 8.11; N, 9.39. Found (avge): C, 69.24; H, 7.96; N, 9.51.

If neodymium trichloride is substituted for scandium trichloride in the above procedure, tris(2-dimethylaminomethylphenyl)neodymium will be the product.

If yttrium trichloride is substituted for scandium trichloride in essentially the process of Example 5, tris(2-dimethylaminomethylphenyl)yttrium will be produced.

If scandium trichloride and 5-t-butyl-2-dimethylaminomethylphenyllithium are used as the starting materials in in the process of Example 5, the product will be tris(5-t-butyl-2-dimethylaminomethylphenyl)scandium.

EXAMPLE 6

This example illustrates the preparation of tris-(2-dimethylaminomethylphenyl)erbium.

To a suspension of anhydrous erbium trichloride (3.0 g, 10.96 mmoles) in ether was added 2-N,N-dimethylaminomethylphenyllithium (4.64 g). After stirring overnight, the solution was filtered. The residue was dissolved in about 200 ml of warm toluene, filtered and the solvent was removed by rotary evaporation to give pink crystals. The yield was 4.34 g of product melting at 160°–161° C.

Anal. Calcd for $C_{27}H_{36}ErN_3$: C, 56.90; H, 6.37; N, 7.37; Er, 29.35. Found: C, 47.83; H, 5.65; N, 6.27; Er, 29.36.

EXAMPLE 7

This example illustrates the preparation of bis-(2-dimethylaminobenzyl)chromium.

To a stirred solution of 2.15 g of anhydrous chromium dichloride in tetrahydrofuran at −78° C was added a solution of 5.0 g of 2-dimethylaminobenzyllithium in about 150 ml of tetrahydrofuran. The solution turned dark green. When the addition was completed, the solution was warmed to room temperature and the color gradually turned dark brown. The mixture was filtered and the filtrate was stripped to dryness by rotary evaporation to give a dark-brown solid. The solid was washed from the flask with pentane. It was dissolved in toluene, the solution was filtered, and pentane was added. The flask was cooled to −40° C to give dark red-brown crystals, which were separated by filtration. The yield of bis(2-dimethylaminobenzyl)chromium was 1.28 g (mp 119°–120° C).

Anal. Calcd. for $C_{18}H_{24}N_2Cr$: C, 67.47; H, 7.55; N, 8.74. Found (avge): C, 63.52; H, 7.24; N, 8.12.

If 2-dipropylaminobenzyllithium is substituted for 2-dimethylaminobenzyllithium in the foregoing example, bis(2-dipropylaminobenzyl)chromium will be formed.

If molybdenum trichloride is substituted for chromium dichloride, the product will be bis(2-dimethylaminobenzyl)molybdenum.

EXAMPLE 8

This example illustrates the preparation of bis(2-dimethylaminomethylphenyl)chromium.

To a stirred suspension of 2.16 g of anhydrous chromium dichloride in tetrahydrofuran at −78° C was added a solution of 5.0 g of 2-dimethylaminomethylphenyllithium in tetrahydrofuran. The color rapidly turned dark orange. When the addition was completed, the mixture was warmed to room temperature and stirred for thirty minutes. It was filtered, and the filtrate was stripped to dryness by rotary evaporation to give a dark-orange solid that was washed from the flask with pentane. The solid was taken up in toluene, the mixture was filtered, pentane was added to the filtrate, and the flask was cooled to −40° C to give dark-orange, crystals. The crystals were separated by filtration, washed with pentane, and dried under vacuum. The yield of bis(2-dimethylaminomethylphenyl)chromium was 2.5 g (mp 190°–191° C).

Anal. Calcd. for $C_{18}H_{24}N_2Cr$: C, 67.47 H, 7.55; N, 8.74; Cr, 16.23. Found (avge): C, 67.60; H, 7.76; N, 9.21; Cr, 14.42.

If 2-dipropylaminomethylphenyllithium is used instead of 2-dimethylaminomethylphenyllithium in essentially the procedure of the foregoing example, the product will be bis(2-dipropylaminomethylphenyl)chromium.

EXAMPLE 9

This example illustrates of the preparation of bis(2-dimethylaminomethylphenyl)molybdenum.

To a stirred suspension of 3.12 g of anhydrous molybdenum trichloride in tetrahydrofuran was added a solution of 6.25 g of 2-dimethylaminomethylphenyllithium in tetrahydrofuran. The mixture was stirred for 40 hours, and the solvent was removed by rotary evaporation. Pentane was added and the mixture was filtered. The solid was taken up in toluene, the mixture was filtered, and hexane was added to the filtrate. The solution was cooled to −40° C overnight to give dark-reddish-green crystals that were separated by filtration and washed with pentane. The yield of bis(2-dimethylaminomethylphenyl)molybdenum was 5.6 g, mp 275° C.

Anal. Calcd. for $C_{18}H_{24}N_2Mo$: C, 59.33; H, 6.64; N, 7.69; Mo, 26.33. Found: C, 59.49; H, 6.28; N, 7.61; Mo, 26.29.

EXAMPLE 10

This example illustrates the preparation of bis-(5-tert-butyl-2-dimethylaminomethylphenyl)molybdenum.

Anhydrous molybdenum trichloride (2.0 g) and 5.85 g of 5-tert-butyl-2-dimethylaminomethylphenyllithium were placed in a flask and 200 ml of ethyl ether was added. The mixture was stirred for 24 hours to give a green-brown solution. The ether was removed by rotary evaporation. Pentane was added, and the mixture was filtered to give a green filtrate and a red solid. The red solid was taken up in pentane, the mixture was filtered, and the solvent was slowly removed from the filtrate by rotary evaporation to give a red crystalline solid. The yield of bis(5-tert-butyl-2-dimethylaminomethylphenyl)molybdenum was 0.45 g (mp 206°–208° C).

Anal. Calcd. for $C_{26}H_{40}N_2Mo$: C, 65.52; H, 8.46; N, 5.88; Mo, 20.13. Found: C, 66.78; H, 8.67; N, 5.95; Mo, 18.59.

EXAMPLE 11

This example illustrates the preparation of tetrakis(2-dimethylaminobenzyl)titanium.

To a solution of 0.038 g of titanium tetrachloride in 3 ml of toluene was added 0.113 g of 2-dimethylaminobenzyllithium. The mixture was stirred for about 5 minutes and filtered to remove lithium chloride. The filtrate was a solution of tetrakis(2-dimethylaminobenzyl)titanium in toluene.

EXAMPLE 12

This example illustrates the preparation of tetrakis(2-dimethylaminobenzyl)zirconium.

To a mixture of 0.046 g of zirconium tetrachloride and 0.113 g of 2-dimethylaminobenzyllithium was added 3 ml of toluene, and the mixture was warmed to about 50° C with stirring. Reaction slowly took place to give an orange liquid. When there was no further appreciable change in the color of the liquid, the mixture was cooled and filtered to give an orange solution of tetrakis(2-dimethylaminobenzyl)zirconium.

EXAMPLE 13

This example illustrates the preparation of tetrakis(2-dimethylaminomethylphenyl)titanium.

To a solution of 0.038 g of titanium tetrachloride and 3 ml of toluene was added 0.113 g of 2-dimethylaminomethylphenyllithium. The mixture was stirred for about 10 minutes at room temperature, during which time the liquid became dark orange. The lithium chloride that had formed was separated by filtration, to give tetrakis(2-dimethylaminomethylphenyl)titanium as a dark-orange solution in toluene.

EXAMPLE 14

This example illustrates the preparation of tetrakis(2-dimethylaminoethylphenyl)zirconium.

To a mixture of 0.046 g of zirconium tetrachloride and 0.113 g of 2-dimethylaminomethylphenyllithium was added 3 ml of toluene. The mixture was stirred for about 15 minutes at room temperature, during which time the liquid became deep orange. The lithium chloride that had formed was separated by filtration to give a deep-orange solution of tetrakis(2-dimethylaminomethylphenyl)zirconium in toluene.

EXAMPLE 15

This example illustrates the polymerization of ethylene in the presence of clay using tris(2-dimethylaminobenzyl)chromium as a catalyst component.

A. Tris(2-dimethylaminobenzyl)chromium was prepared as follows:

To a stirred suspension of 3.15 g of anhydrous chromium trichloride in tetrahydrofuran was added 8.47 g of 2-dimethylaminobenzyllithium. The solution became warm and turned dark orange. After stirring for 15 minutes the solvent was removed by rotary evaporation and the solids were washed from the flask with ethyl ether. The dark red crystals were dissolved in dichloromethane, the mixture was filtered, and the solvent was removed by rotary evaporation to give dark red crystals that were washed from the flask with ethyl ether. The yield of tris(2-dimethylaminobenzyl)chromium was 7.50 g (mp 167°-168° C).

Analyses were carried out on a separate sample of the product, prepared by essentially the foregoing procedure but with ethyl ether as the medium in place of tetrahydrofuran.

Anal. Calcd. for $C_{27}H_{36}N_3Cr$: C, 71.33; H, 7.98; N, 9.25. Found (avge): C, 70.05; H, 7.93; N, 9.92. Electronic spectrum ($CH_2Cl_2$): 656 nm; $\epsilon$, 80. 745 nm; $\epsilon$, 84.

B. Ethylene was polymerized in the presence of tris(2-dimethylaminobenzyl)chromium as follows:

Two liters of reagent-grade cyclohexane was passed through a 3-inch bed of Woelm acid alumina into a 5-liter round-bottom flask fitted with a blender in its base. Stirring was started, and 7.5 mmol of triisobutylaluminum was added from a syringe, followed after 10–15 seconds by 185 g of "Harwick" GK kaolinite clay that had been dried at 258° C for 15 hours in a stream of nitrogen and cooled under nitrogen. After stirring for 1 minute, a solution of 0.2 mmol (90 mg) of tris(2-dimethylaminobenzyl)chromium in 6 ml of toluene was added from a syringe. The suspension was stirred for five minutes and transferred through polyethylene tubing under nitrogen pressure to a dry, oxygen-free, ordinary-steel autoclave equipped with a stirrer. The stirrer was run at 1000 rpm during the addition and the polymerization. The autoclave was heated to 60° C, the nitrogen was replaced by ethylene at 100 psi, and the system was heated at 60° C and 100 psi, ethylene being added to maintain this pressure, until 86 g of ethylene had been added in addition to the amount used initially to reach 100 psi (40 g). The aim was to consume 90 g of ethylene and to form an approximately 67/33 clay/polyethylene composition. The time required was 1.00 hr. The autoclave was immediately vented to atmospheric pressure and cooled, and the solid composition was separated by filtration and air dried to give 264.7 g of powder that passed a 20-mesh screen plus 31.6 g of coarser material.

A portion of the powder was added to a $CHBr_3$:$CCl_4$ mixture (1:1 by weight); all the powder floated, indicating that no unattached clay particles were present, i.e., that all the clay particles had been coated with polyethylene. In a similar test with $CCl_4$:n-$C_3H_7OH$ (3:2 by volume), all the powder sank, indicating that no clay-free polyethylene was present. The product gave 51.06% ash on combustion, corresponding to a clay content of 59.4%. The inherent viscosity of the polyethylene was 12.1 (0.05 w/v % in 1,2,4-trichlorobenzene). Physical properties of molded objects are reported in Table I.

C. In a control experiment in which no chromium compound was added and which was run at 100 psi for 0.57 hr, 200 psi for 0.52 hr, and 300 psi for 2.43 hr, the product contained 91.5% clay, i.e., only 8.5% polyethylene.

EXAMPLES 16 to 28

A. By essentially the procedure of Example 15, polyethylene/clay composites were made with other catalysts in place of tris(2-dimethylaminobenzyl)chromium. These runs, together with the properties of the products, are summarized in Table I. In several runs, as noted in the third column, triethylaluminum ($Et_3Al$) was used in place of triisobutylaluminum ($iBu_3Al$). Also in several runs, as noted in the fourth column, pressures higher than 100 psi were used. Except as indicated in the footnotes, each run was continued until about 90 g of ethylene had reacted.

B. Tris(5-t-butyl-2-dimethylaminomethylphenyl)chromium, used in Example 16 was prepared as follows:

Anhydrous chromium trichloride (2.0 g) and 5-t-butyl-2-dimethylaminomethylphenyllithium (7.48 g) were placed in a flask and ether was added. The solution turned orange, and after stirring for two hours the mixture was filtered. The ether was removed by rotary evaporation to give an oil. A small amount of pentane was added which caused the oil to crystallize. The crystals were washed from the flask with pentane and dried in vacuo. An analytical sample was recrystallized from hexane. The yield of tris(5-tert-butyl-2-dimethylaminomethylphenyl)chromium was 5.20 g (mp 224°-225° C).

Anal. Calcd. for $C_{39}H_{60}CrN_3$: C, 75.19; H, 9.71; N, 6.75; Cr, 8.35. Found: C, 75.79; H, 9.63; N, 6.81; Cr, 7.63.

C. Tris(2-dimethylaminomethylphenyl)chromium, used in Example 17 was prepared as follows:

To a suspension of chromium trichloride (2.0 g) in tetrahydrofuran was added a solution of 2-dimethylaminomethylphenyllithium in tetrahydrofuran. An orange solid precipitated immediately. After stirring for one hour the mixture was filtered and the solid was washed with tetrahydrofuran and ethyl ether. The yield of tris(2-dimethylaminomethylphenyl)chromium was 5.63 g (mp >300° C).

Anal. Calcd. for $C_{27}H_{36}CrN_3$: C, 71.33; H, 7.98; N, 9.75. Found: C, 70.30; H, 7.90; N, 9.21.

TABLE I
POLYMERIZATION OF ETHYLENE ON CLAY

| Ex. | Catalyst | Mmol $R_3Al$: mmol Catalyst | Polym'n., psi/hr. | % Filler | Polymer inh. visc. | $T_{max}$, psi | $E_b$, % | $M_p$, Kpsi | Impact Strength Gardner, in lb. 25° C | Impact Strength Gardner, in lb. −40° C | Izod, ft.lb/in. of notch, 0° F. |
|---|---|---|---|---|---|---|---|---|---|---|---|
| 15 | Tris(2-dimethylaminobenzyl)chromium | iBu₃Al 7.5:02 | 100/1.00 | 59.4 | 12.1 | 2825 / 2799 | 14.8 / 25.0 | 637 / 641 | 105 | — | 0.88 / 0.82 |
| 16 | Tris(5-t-butyl-2-dimethylaminomethylphenyl)chromium | iBu₃Al 7.5:0.2 | 100/0.38 | 59.7 | 10.7 | 2836 / 2895 | 14 / 45 | 645 / 667 | >240 / 130 | 40 | 1.06 / 1.02 |
| 17 | Tris(2-dimethylaminomethylphenyl)chromium (added as solid) | Et₃Al 7.5:0.2 | 100/1.03 | 58.6 | 11.4 | 2827 / 2818 | 42 / 322 | 809 / 622 | >240 | — | 4.97 / 4.02 |
| 18 | Tris(2-dimethylaminobenzyl)scandium | iBu₃Al 7.5:0.2 | 100/0.2 | 64.4 | 21.4 | 2720 / 2717 | 333 / 261 | 631 / 625 | 141 | 125 | 5.45 / 5.33 |
| 19 | Tris(2-dimethylaminobenzyl)erbium | iBu₃Al 7.5:0.2 | 100/1.85 | 69.5 | 20.0 | 2881 / 2774 | 59 / 224 | 848 | >240 | 100 | 2.00 / 2.11 |
|  |  | iBu₃Al 7.5:0.2 | 100/0.48 200/0.15 300/0.77 400/0.90 500/1.14 | 83.0* | 16.0 | — | — | — | — | — | — |
|  |  | Et₃Al 7.5:0.2 | 200/0.48 300/0.70 400/2.00 | 81.0* | 16.6 | — | — | — | — | — | — |
|  |  | iBu₃Al 7.5:0.2 | 100/0.42 200/0.52 300/0.60 | 62.0 | 12.4 | 2577 / 2679 | 421 / 281 | 555 / 617 | >240 | >160 | 5.21 / 7.59 |
| 20 | Tris(2-dimethylaminomethylphenyl)scandium (added as solid) | Et₃Al 7.5:0.2 | 100/0.27 | 65.5 | 19.4 | 3096 / 3001 | 237 / 326 | 590 / 697 | 174 | 140 | 5.79 / 5.89 |
| 21 | Tris(2-dimethylaminomethylphenyl)erbium | iBu₃Al 7.5:0.2 | 100/3.0 | 66.5 | 17.0 | 2670 / 2848 | 340 / 148 | 761 / 793 | >240 | >160 | 3.19 / 3.77 |
|  |  | iBu₃Al 5.0:0.2 | 100/2.38 | 65.0 | 12.8 / 13.6 | 2664 / 2658 | 18 / 306 | 583 / 575 | >240 | 130 | 6.08 / 5.82 |
|  |  | iBu₃Al 7.5:0.2 | 100/0.25 200/0.55 300/2.42 | 69.5 | 20.5 | 2993 / 2993 | 1.2 / 1.6 | 890 / 989 | 135 | — | 0.67 / 0.61 |
| 22 | Bis(2-dimethylaminobenzyl)chromium | iBu₃Al 7.5:0.2 | 100/1.25 | 67.5 | 21.6 | 3219 / 3098 | 2.0 / 1.2 | 884 / 860 | 95 | — | 0.50 / 0.51 |
| 23 | Bis(2-dimethylaminomethylphenyl)chromium | Et₃Al 7.5:0.2 | 100/0.38 | 69.2 | 10.0 | 3171 / 1304 | 0.75 / 0.90 | 1073 / 496 | 86 | <10 | 0.55 / 0.58 |
| 24 | Bis(2-dimethylaminomethylphenyl)molybdenum | iBu₃Al 7.5:0.1 | 100/0.2 200/0.3 300/2.68 | 87.0 | — | — | — | — | — | — | — |
| 25 | Tetrakis(2-dimethylaminobenzyl)titanium | Et₃Al 7.5:0.2 | 100/0.40 200/1.75 | 67.6 | 19.22 | 3296 / 3125 | 8.6 / 37.9 | 751 / 765 | 180 | 80 | 1.54 / 1.38 |
| 26 | Tetrakis(2-dimethylaminobenzyl)zirconium | Et₃Al 7.5:0.2 | 100/0.47 200/0.55 300/1.07 | 55.5 | 19.79* | 2785 / 3119 | 103 / 552 | 714 / 833 | >240 | 160 | 15.33 / 15.21 |
| 27 | Tetrakis(2-dimethylaminomethylphenyl)titanium | Et₃Al 7.5:0.2 | 100/0.63 200/0.57 300/0.68 400/1.42 | 62.6 | 21.74 | 2791 / 2746 | 390 / 431 | 567 / 910 | >240 | 120 | 8.26 / 7.09 |
| 28 | Tetrakis(2-dimethylaminomethylphenyl)zirconium | Et₃Al 7.5:0.2 | 150- 100/0.48-** 100/1.05 | 56.2 | 17.08 | 2972 / 3180 | 463 / 41 | 472 / 605 | >240 | <160 | 14.03 / 13.97 |

*Determined at 0.025% concentration in 1,2,4-trichlorobenzene.
**Ethylene was overpressured to 150 psi; no more ethylene was added until consumption of ethylene had reduced the pressure to 100 psi.

EXAMPLES 29-33

By essentially the same procedure as Example 15, some of the catalysts were used to make polyethylene/alumina trihydrate composites. The results are summarized in Table II. Two hundred grams of "Alcoa" C-30BF alumina trihydrate, dried at 150°-175° C, was used in each run, the objective being to make an approximately 69/31 alumina trihydrate/polyethylene product. The polymerization temperature was 50° C.

TABLE II
POLYMERIZATION OF ETHYLENE ON ALUMINA TRIHYDRATE

| Ex. | Catalyst | Mmol R₃Al: mmol catalyst | Polym'n, psi/hr. | % mineral | Polymer inh. visc. | $T_{max}$, psi | $E_b$, % | $M_p$, Kpsi | Impact Strength Gardner, in lb. 25° C | Gardner -40° C | Izod, ft. lb/in. of notch 0° F |
|---|---|---|---|---|---|---|---|---|---|---|---|
| 29 | Tris(2-dimethylamino-benzyl)chromium | iBu₃Al 3.0:0.2 | 200/1.23 | 69.2 | 17.9 | 1658 1651 | 44 36 | 546 761 | 45 | — | 0.90 0.97 |
| 30 | Tris(2-dimethylamino-benzyl)scandium | Et₃Al 5.1:0.3 | 300/0.53 | 68.9 | 26.8 | 2408 2485 | 394 434 | 558 529 | >210 <240 | 135 | 6.45 6.24 |
| 31 | Tris(5-t-butyl-2-dimethylaminomethyl-phenyl)chromium | iBu₃Al 3.5:0.2 | 400–450/3.58 | 67.2 | — | 1713 1738 | 33 37 | 567 635 | 50 | — | 1.49 1.47 |
| 32 | Tris(2-dimethylamino-methylphenyl)scandium (added as solid) | Et₃Al 5.1:0.3 | 100/1.19 | 76.7 | 22.3 | 2193 2079 | 356 313 | 605 543 | 100 | 90 | 5.79 5.89 |
| 33 | Tris(2-dimethylamino-methylphenyl)erbium | Et₃Al 5.1:0.3 | 100/0.85 200/0.63 300/0.62 400/1.77 | 84.5 | — | — | — | — | — | — | — |
|  |  | iBu₃Al 3.5:0.2 | 265–270/0.63 283–310/2.43 | 80.7 | — | 1384 1410 | 242 261 | 628 731 | 55 | — | 3.52 3.31 |

EXAMPLE 34

This example illustrates the polymerization of ethylene in the absence of particulate filler compound using tris(2-dimethylaminomethylphenyl)scandium as a catalyst component.

Two liters of cyclohexane (reagent grade) was passed through 3 inches of Woelm acid alumina, supported in a sintered glass funnel, into a 5-liter round bottom flask with a Waring blendor in the base. A solution of 3.0 mmol of triethylaluminum in 3.0 ml of heptane was added via a syringe transfer, followed by stirring for 10–15 seconds. Next 1.0 mmol (448 mg) of tris(2-dimethylaminomethylphenyl)scandium as a powder was added to the flask; this addition was followed by 10 minutes of vigorous stirring. The resulting mixture was next transferred to a 1 gal. ordinary steel autoclave in a nitrogen atmosphere; transfer was made within 15–30 minutes of the addition of the scandium compound. The autoclave stirrer was rotated at a speed of 1,000 rpm during the transfer and during the polymerization. The autoclave contents were heated to 50° C and the nitrogen atmosphere replaced by ethylene at 100 psi pressure; 40 g of ethylene was added. After 15 minutes 20 g of ethylene was absorbed, but since no more reacted after an additional 9 minutes, the ethylene pressure was raised to 200 psi and held there for 1.33 hrs; no additional ethylene reacted. Ethylene pressure was then raised to 300 psi and the temperature to 60° C, and held there for 1.6 hr during which an additional 70 g of ethylene was absorbed. Temperature was maintained at 50° C and 60° C during the polymerization by water in cooling coils. The autoclave gases were immediately vented and the contents cooled to ordinary temperature. The solid polymer produced stuck to the stirrer and sides of flask, and was removed by cutting with a knife and scraping. There were losses, but 72.6 g of polymer was recovered after air drying over the week end. A small film was pressed from the polymer at approximately 145° C and 2000 psi pressure; the resulting film was very strong. The polymer had an inherent viscosity of 16.9.

EXAMPLE 35

The experiments in this example demonstrate the sensitivity of the products of the invention to oxygen, which is the basis for their utility as oxygen-scavenging agents.

In each experiment, about 0.01 g of the indicated product was placed in a vial under nitrogen, following which toluene was added to dissolve at least some of the material. Dry oxygen was then injected into the liquid through a serum cap. In each experiment a rapid change in color was observed, corresponding to a rapid reaction of the particular product with oxygen. The compounds that were used and the observations that were made are summarized in the following table:

| Product of Example No. | Original Color of Solution | Color After Injection of Oxygen |
|---|---|---|
| 3 | yellow | colorless |
| 4 | yellow | colorless |
| 15A | red | brown |

I claim:
1. Transition metal compounds of the formulae

$$M^1A_3 \quad (1)$$

wherein $M^1$ = Sc, Y or a rare earth metal, and

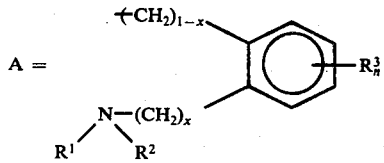

$$A =$$

where $x = 0$ or $1$ $R^1$, $R^2$ and the $R^3$'s are each $C_1$–$C_8$ alkyl, and $n = 0, 1, 2, 3$ or $3 + x$, when $x = 0$, the position in the benzene ring adjacent to the —NR¹R² substituent, other than that occupied by the —CH₂— substituent, being unsubstituted, $$M^2A_2 \quad (2)$$

wherein

UNITED STATES PATENT OFFICE
CERTIFICATE OF CORRECTION

PATENT NO. : 4,057,565
DATED : November 8, 1977
INVENTOR(S) : Leo Ernest Manzer

It is certified that error appears in the above-identified patent and that said Letters Patent are hereby corrected as shown below:

Column 14, line 12, the comma should be deleted.

Column 21, line 13 (claim 2, line 3), formula (1) should read --$M^1A_3$.--

Signed and Sealed this

Twenty-eighth Day of March 1978

[SEAL]

Attest:

RUTH C. MASON
Attesting Officer

LUTRELLE F. PARKER
Acting Commissioner of Patents and Trademarks